(12) United States Patent
Edinger et al.

(10) Patent No.: US 7,232,997 B2
(45) Date of Patent: Jun. 19, 2007

(54) APPARATUS AND METHOD FOR INVESTIGATING OR MODIFYING A SURFACE WITH A BEAM OF CHARGED PARTICLES

(75) Inventors: Klaus Edinger, Heppenheim (DE); Josef Sellmair, Reinheim (DE); Thorsten Hofmann, Rodgau (DE)

(73) Assignee: NaWoTec GmbH, Rossdorf (DE)

( * ) Notice: Subject to any disclaimer, the term of this patent is extended or adjusted under 35 U.S.C. 154(b) by 0 days.

(21) Appl. No.: 11/106,368

(22) Filed: Apr. 14, 2005

(65) Prior Publication Data

US 2005/0230621 A1    Oct. 20, 2005

Related U.S. Application Data

(60) Provisional application No. 60/563,351, filed on Apr. 19, 2004, provisional application No. 60/563,177, filed on Apr. 16, 2004.

(30) Foreign Application Priority Data

Apr. 15, 2004   (EP)   ................................. 04008972

(51) Int. Cl.
*G01N 23/00*   (2006.01)

(52) U.S. Cl. ...................... 250/311; 250/310; 250/306; 250/307; 250/309

(58) Field of Classification Search ...................... None
See application file for complete search history.

(56) References Cited

U.S. PATENT DOCUMENTS 4,818,872 A    4/1989   Parker et al.
4,992,661 A    2/1991   Tamura et al.

(Continued)

FOREIGN PATENT DOCUMENTS

DE    35 45 350 A1    7/1984

(Continued)

OTHER PUBLICATIONS

Hans W.P. Koops, M. Weber, C. Schossler and A. Kaja; "Three-Dimensional additive electron-beam lithography"; Metal/Nonmetal Microsystems: Physics, Technology, and Applications, SPIE Proceedings—The International Society for Optical Engineering, Apr. 1996; pp. 388-395; vol. 2780.

(Continued)

*Primary Examiner*—Jack I. Berman
*Assistant Examiner*—Zia R. Hashmi
(74) *Attorney, Agent, or Firm*—Meyertons Hood Kivlin Kowert & Goetzel, P.C.; Jeffrey C. Hood

(57) ABSTRACT

An apparatus for investigating and/or modifying a sample with charged particles, in particular a scanning electron microscope, is provided. The apparatus comprises a beam (1, 2) of charged particles, a shielding element (10) having an opening (30) for the beam of charged particles to pass through, wherein the opening (30) is sufficiently small and the shielding element (10) sufficiently closely positioned to the surface (20) of the sample to reduce the influence of charge accumulation effects at the surface on the beam of charged particles.

36 Claims, 4 Drawing Sheets

U.S. PATENT DOCUMENTS

| | | |
|---|---|---|
| 5,591,971 A | 1/1997 | Shahar et al. |
| 6,344,750 B1 | 2/2002 | Lo et al. |
| 6,373,054 B2 | 4/2002 | Hiroi et al. |
| 6,512,228 B2 | 1/2003 | Todokoro et al. |
| 6,570,154 B1 | 5/2003 | Masnaghetti et al. |
| 6,586,736 B1 * | 7/2003 | McCord ............... 250/310 |
| 6,664,546 B1 | 12/2003 | McCord et al. |
| 6,683,320 B2 | 1/2004 | Gerlach et al. |
| 6,979,822 B1 * | 12/2005 | Stewart et al. ......... 250/310 |
| 2004/0169141 A1 * | 9/2004 | Adamec et al. ......... 250/310 |
| 2005/0103272 A1 | 5/2005 | Koops et al. |

FOREIGN PATENT DOCUMENTS

| | | |
|---|---|---|
| DE | 44 12 415 A1 | 10/1994 |
| DE | 102 08 043 A1 | 8/2003 |
| EP | 0 884 759 A1 | 12/1998 |

OTHER PUBLICATIONS

International search report for application No. PCT/EP2005/004036 mailed Jun. 15, 2005.

* cited by examiner

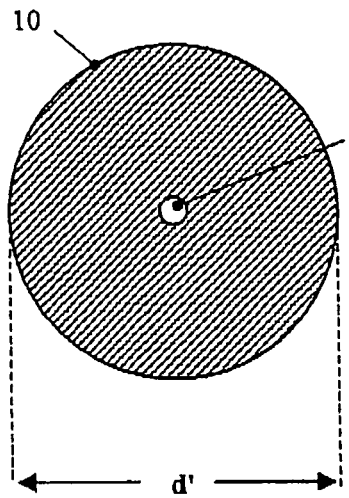
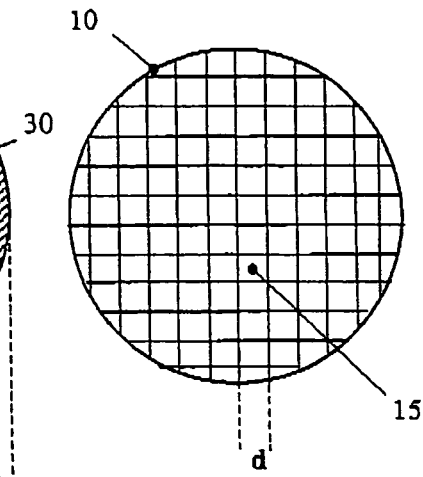
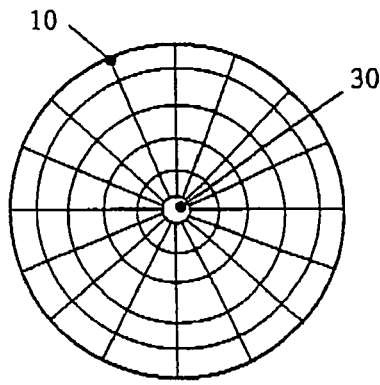
Fig. 5a   Fig. 5b   Fig. 5c
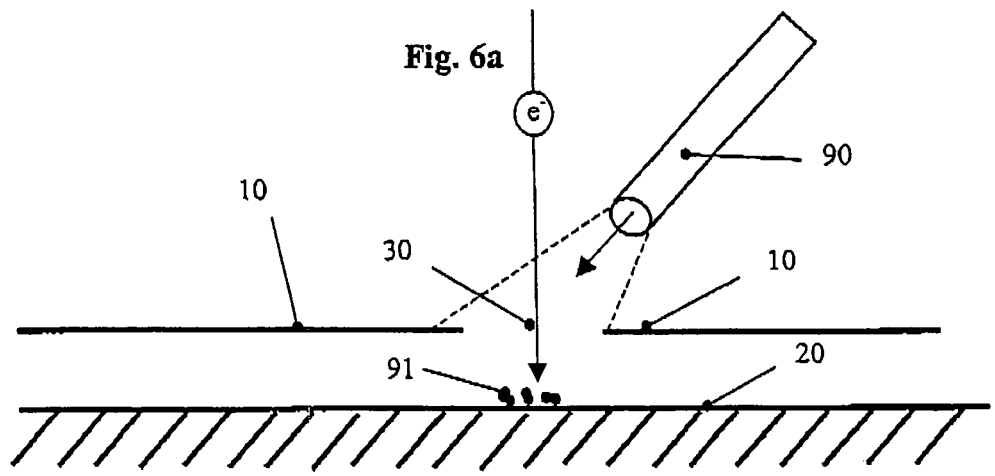
Fig. 6a

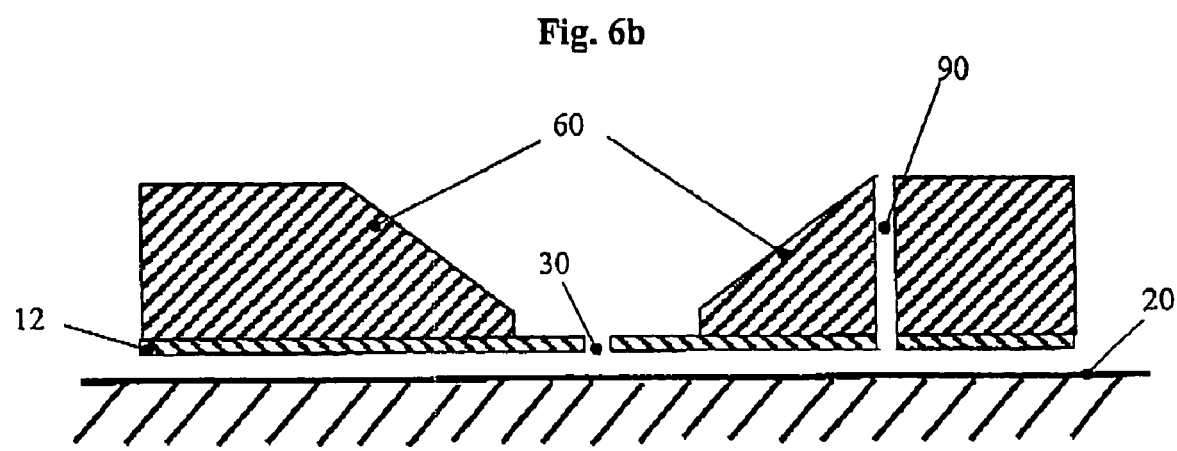

APPARATUS AND METHOD FOR INVESTIGATING OR MODIFYING A SURFACE WITH A BEAM OF CHARGED PARTICLES

PRIORITY CLAIM

This application claims benefit of priority of U.S. Provisional Application Ser. No. 60/563,177 titled "Apparatus and Method For Investigating or Modifying a Surface with a Beam of Charged Particles", filed Apr. 16, 2004, whose inventor is Klaus Edinger.

This application claims benefit of priority of U.S. Provisional Application Ser. No. 60/563,351 titled "Apparatus and Method For Investigating or Modifying a Surface with a Beam of Charged Particles", filed Apr. 19, 2004, whose inventor is Klaus Edinger.

TECHNICAL FIELD

The present invention relates to an apparatus and a method using one or more charged particle beams for the investigation and/or modification of a sample. In particular, the invention concerns the investigation and/or modification of sample surfaces by low voltage scanning particle beams, for example in a scanning electron microscope.

DESCRIPTION OF THE RELATED ART

In many microscopy techniques such as scanning electron or scanning ion microscopy, a focussed beam of charged particles is scanned across the sample. The particles, which are emitted or scattered from the sample, are collected by a detector to provide a two-dimensional image. Scanned beams of particles, in particular electrons, are also used for modifying the surface, for example by selectively removing or depositing material onto a sample surface. Such a technique is for example described in the publication "Three-dimensional additive electron-beam lithography" in SPIE Vol. 2780 p. 388 of Koops et al. and in the DE 102 08 043 A1. The selective deposition or removal of material with a high resolution is of particular interest for the repair of masks used in the semiconductor industry.

It is common knowledge that charging effects can significantly impair the image quality of a scanning electron microscope, in particular when imaging electrically isolating features of a sample. The impinging beam of charged particles (primary beam) causes areas of the sample surface to charge to arbitrary voltages, depending on the properties and the polarity of the primary beam and on the amount and polarity of the secondary particles (forming the so called secondary beam), which are generated by the primary beam. The resulting charge distributes across the sample surface in a manner depending on its geometry and structure with its insulating and conductive regions as well as on electrical properties of areas surrounding the sample The surface charges in turn lead to a deformation (e.g. defocusing, stigmation) and a deflection (e.g. image drift, image distortion) of the focused primary beam. The image drift is the most severe problem of high precision scanning electron microscopy for metrology applications such as CD-SEM (scanning electron microscopy for the measurement of critical dimensions), since it depends on the geometry of conductive or non-conductive features on the sample. This structure can vary from sample to sample, from field of view (FOV) to FOV, and from one set of sample material composition to another.

Furthermore, the amount of secondary electrons and their trajectories are affected by the surface charges. Since the amount of secondary electrons collected by a detector is used to determine the local brightness of the generated image, the contrast of the images is also affected by surface charging. In particular in cases where high positional accuracy is requested, such as the inspection of masks or wafers by scanning electron microscopy, charging effects limit the accuracy of the measurement of electrically isolated features. Especially low voltage electron microscopy is suffering from charge accumulation effects, since the primary beam is more susceptible to electrical fields in their respective paths compared to high voltage electron microscopy.

In order to overcome this problem, various approaches have been developed in the prior art to eliminate undesired charge accumulation or at least to reduce its effects:

One commonly used solution of the problem of charge accumulation on insulating objects is the application of a conductive layer on the sample surface. However, applying such a layer is not always possible and even excluded for several applications in the semiconductor industry. Another method is to additionally provide a further beam of charged particles to deliver opposite charges to the sample, for example using charge neutralizing electron flood guns in systems for FIB (Focused Ion Beam). A further method is to apply proper electric potentials near the sample surface to prevent secondary electrons from escaping the sample surface, thus inhibiting an excessive positive charge build-up. Yet another method is to vary scan conditions in order to vary charging conditions and to avoid excessive asymmetrical charging.

Some methods to overcome the problems related to accumulation of charges are described in more detail in following list of prior art patents and publications:

U.S. Pat. No. 4,818,872 discloses a system in which neutralizing electrons from a flood gun are directed by deflection elements below the final lens onto the sample. U.S. Pat. No. 6,683,320 addresses the problem of focussing and positioning of a focussed ion beam onto an insulating sample. A neutralizing electron beam is disclosed, which is passed through the final lens for neutralization of at least a portion of the accumulated positive charge of the sample.

U.S. Pat. No. 6,344,750 addresses the problem of asymmetrical charging, resulting in image distortions and image contrast variations in scanning electron microscope images. The solution disclosed in this patent consists of a two-fold scan procedure, one to charge the surrounding area of the image field and a second to scan the image field itself.

U.S. Pat. No. 6,570,154 addresses the charging of different areas of an insulating sample by the primary electron beam of a scanning electron microscope. A solution is disclosed which multiplexes between two different scan conditions, one having the intention to acquire an image, the other to control charge build-up.

U.S. Pat. No. 6,586,736 addresses the problem of charging effects of insulating samples affecting secondary particle detection efficiency and darkening of the scan field during continuous scanning due to charge accumulation. A solution is presented using voltages applied to electrodes above the target in order to suppress excessive positive charge build-up and to generate a clear image. It is an active scheme acting on the trajectories of secondary particles emitted from the sample surface. A negative voltage is applied to the electrode such that at least some of the emitted particles (e.g., secondary electrons) from the surface are repelled away from the electrode back towards the surface to cancel positive charge that has accumulated on the surface. The applied voltage is being actively adjusted depending on the distance of the primary beam scan from the center of the electrode.

U.S. Pat. No. 6,664,546 addresses the problem of optimizing image quality of a scanning electron microscope by measuring sample surface charge and calculating a set of SEM parameters for optimum operating conditions.

German Patent DE 44 12 415 A1 of Advantest Corp., referenced in U.S. Pat. Nos. 6,664,546 and 6,586,736, discloses a method of using saddle point potentials to control excessive charge accumulation.

All of these approaches are very complicated, either with respect to the necessary instrumentation, which has to be added to the overall apparatus and/or with respect to the process steps necessary to acquire an image. In addition, none of the prior art techniques is capable to fully remove the effects of surface charging on the resulting image.

It is therefore the problem underlying the present invention to provide an apparatus and a method, which allow in an easy and therefore cost-efficient manner to investigate and/or to modify a sample surface with charged particles, wherein the above explained problems related to surface charge accumulation are overcome.

SUMMARY OF THE INVENTION

According to a first aspect, the present invention relates to an apparatus for investigating and/or modifying a sample with charged particles, in particular a scanning electron microscope, comprising a beam of charged particles, a shielding element having an opening for the beam of charged particles to pass through, wherein the opening is sufficiently small and the shielding element sufficiently closely positioned to the surface of the sample to reduce the influence of charge accumulation effects at the surface on the beam of charged particles.

According to the present invention, a shielding element with an opening forming a kind of aperture is preferably kept at a fixed electrical potential and positioned in the very vicinity of the irradiated sample surface. In a preferred embodiment, the distance between the shielding element and the surface is $\leq 250$ μm, preferably $\leq 100$ μm, even more preferably $\leq 50$ μm and most preferably $\leq 10$ μm. However, the shielding element can also directly contact the surface of the sample, although this is in most cases not desirable to avoid an unintended damaging of the sample surface.

The opening has preferably a geometry, which allows a sufficient field of view (FOV), i.e. the primary and/or secondary beam paths remain substantially unobstructed in this area. In a preferred embodiment, the opening has a diameter d, wherein $d \leq 150$ μm, preferably $\leq 100$ μm, even more preferably $\leq 50$ μm and most preferably $\leq 10$ μm. The diameter of the opening is preferably greater or equal to the distance between the opening and the sample surface. In a preferred embodiment the shielding element has a thickness of $\leq 100$ μm, preferably 10–50 μm and more preferably $\leq 10$ μm.

Outside the FOV, the shielding element of the present invention shields the electric field caused by charges accumulating at the sample surface. To this end, the shielding element has preferably an outer dimension of $\geq 0.2$ mm, preferably $\geq 2$ mm, more preferably $\geq 5$ mm and most preferably $\geq 10$ mm. Without shielding, these charges would form an electric field penetrating the path of the primary beam and thus deflect its impact position as well as influence the emission properties of the secondary beam. Using the present invention, the electrical field, caused by the surface charges, essentially terminates at the surface of the shielding element. The geometry of the opening in the shielding element and its distance to the sample can be chosen such that a reduction to an essentially zero charge accumulation effect is accomplished.

Since the basic principle of the present invention is to provide a passive shielding of electrical fields generated by charge built-up and not the active influencing of the trajectories of primary or secondary beams, the shielding element can be kept at any fixed electrical potential without impairing its effectiveness and does not have to be grounded, although a grounded shielding element is clearly encompassed.

In a first embodiment the opening of the shielding element has a substantially circular shape. In an alternative embodiment the beam is scanned over the surface and the opening of the shielding element has a shape corresponding to the part of the surface, which is scanned, for example a substantially rectangular or hexagonal or triangular shape. In yet another embodiment the opening has a slit-like shape, wherein the slit has a width d, for which preferred values were indicated above. This embodiment is especially valuable in electron beam raster scan writing tools, which are employed in the semiconductor process industry.

In a particularly preferred embodiment of the present invention, the shielding element comprises a conductive grid, wherein the grid has preferably a mesh with more than 200 pitch per inch, preferably more or equal to 700 pitch per inch, and/or a transmissivity T of $30\% \leq T \leq 80\%$ and/or a thickness of 1–30 μm. Such a shielding element facilitates the (optical) orientation of the operator on the sample surface, which can be inspected through the (semi-) transparent grid.

In another embodiment the shielding element comprises a conductive membrane, wherein the opening in the membrane has preferably been produced by micro-machining methods such as electron beam lithography, focussed ion beam techniques (FIB), laser beam micro-machining or MEMS.

Further devices are preferably integrated into the shielding element, for example a distance sensor and/or one or more gas supplies. The latter are particularly advantageous, if the sample surface is not only to be observed but also to be modified, for example by electron beam induced chemical reactions.

Further advantageous modifications of the described apparatus form the subject matter of further dependent claims.

According to a further aspect, the present invention relates to a method for investigating and/or modifying a surface with an apparatus as described above. Preferably, the method is used for the repair of a mask, preferably by selective removal and/or deposition of material from or on the mask, respectively. In a further embodiment, the apparatus according to the present invention is used for CD-SEM in order to provide exact references for the investigation of masks and/or semiconductor products.

BRIEF DESCRIPTION OF THE DRAWINGS

In the following detailed description presently preferred embodiments are described with reference to the drawings, which show:

FIGS. 5a–c: three different embodiments for a shielding element; and

FIGS. 6a, 6b: further embodiments of the present invention comprising a gas supply for electron-beam induced deposition of material.

DETAILED DESCRIPTION OF THE EMBODIMENTS

In the following, presently preferred embodiments of the invention are described with particular reference to a scanning electron microscope. However, it is to be understood that the present invention can be used for any apparatus, wherein electrically charged particles are used to study, image or modify a sample either on its surface or in its interior regions. A particular important field of use, which is further described below with reference to FIGS. 6a and 6b, is the repair of masks for the semiconductor industry, Here, the scanned electron beam is used to selectively deposit or remove material from the surface of the mask.

Figure 1:
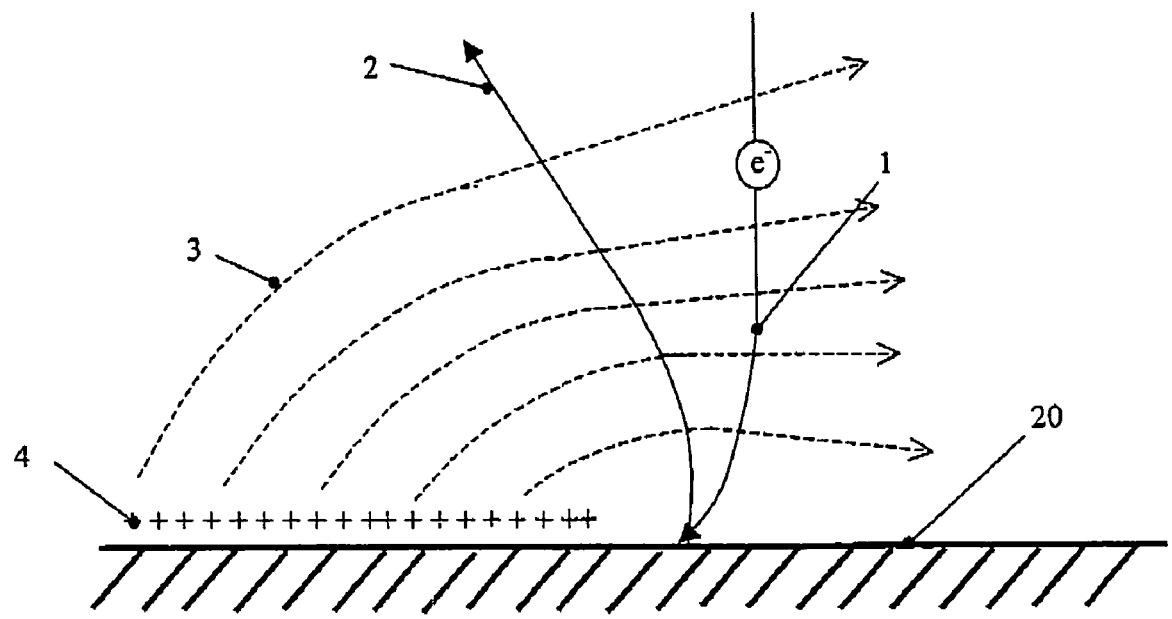
FIG. 1: A schematic representation of the surface charges and their influ-ence on the primary and secondary beam of charged particles with-out the present invention.

FIG. 1 illustrates the problem typically encountered in scanning electron microscopy, in particular with electrons of low energy: Charge distribution 4 is built up at the surface of a sample 20 by charge deposition of a primary beam 1 (negative charging), and by charged particle emission in a secondary beam 2 (positive charging). FIG. 1 shows an example of positive charging. Events of "higher order", such as secondary electrons landing on the sample surface 20 away from the primary beam landing point or secondary particles hitting a surface and releasing further particles do also contribute to the local and temporal charge distribution 4 on the sample surface 20. In addition, conducting or partially conducting features extending from the FOV to outside regions will lead to an inhomogeneous charge distribution 4.

The accumulated charge distribution 4 can be symmetric or asymmetric, the first influencing mainly focus properties of the primary beam 1 and brightness of image, the second influencing primary beam shape (e.g. stigmation) and primary beam deflection (e.g. image distortion and image drift). FIG. 1 illustrates in a substantially simplified manner the influence of the charge distribution 4 on the trajectories of the primary beam 1 and the secondary beam 2 due to the electric field 3.

Figure 2:
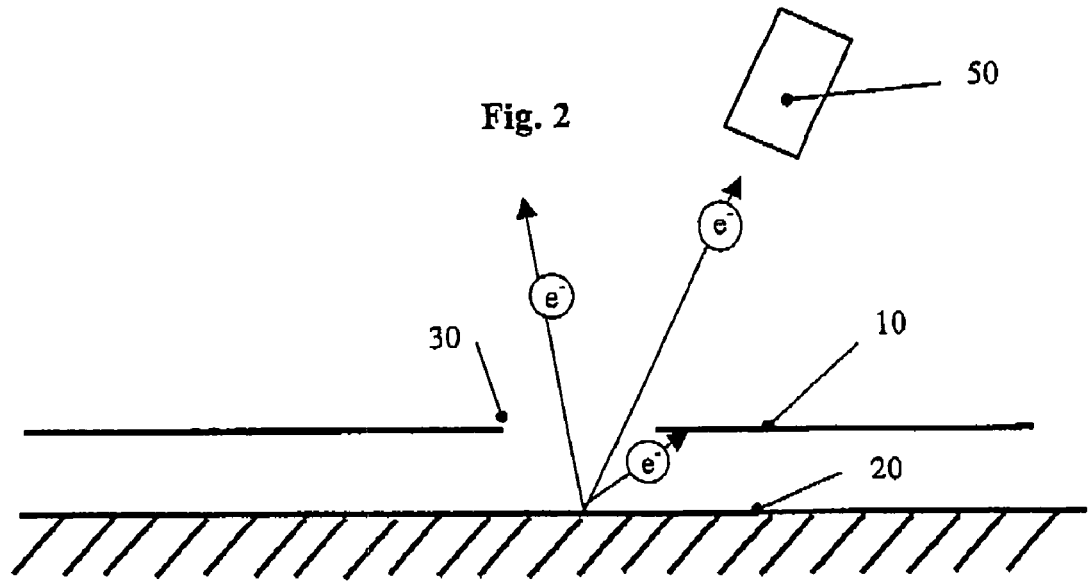
FIG. 2: a schematic representation of an embodiment of the present inven-tion to illustrate the underlying physical principle.
Figure 3:
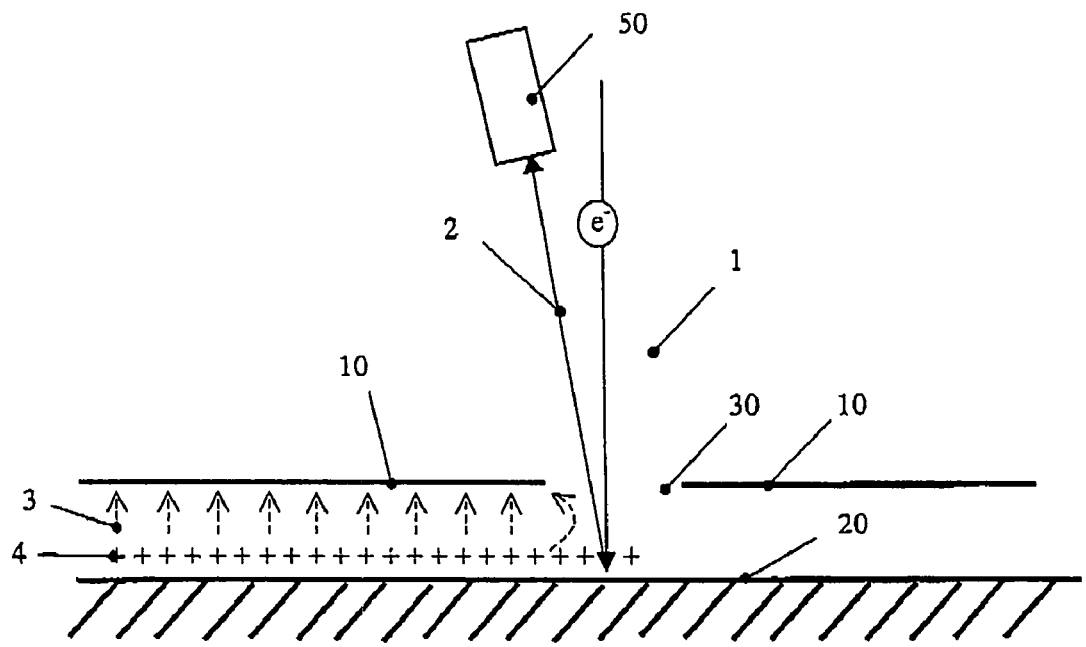
FIG. 3: a schematic representation of the shielding effect for the surface charge in an embodiment of the present invention.
Figure 4:
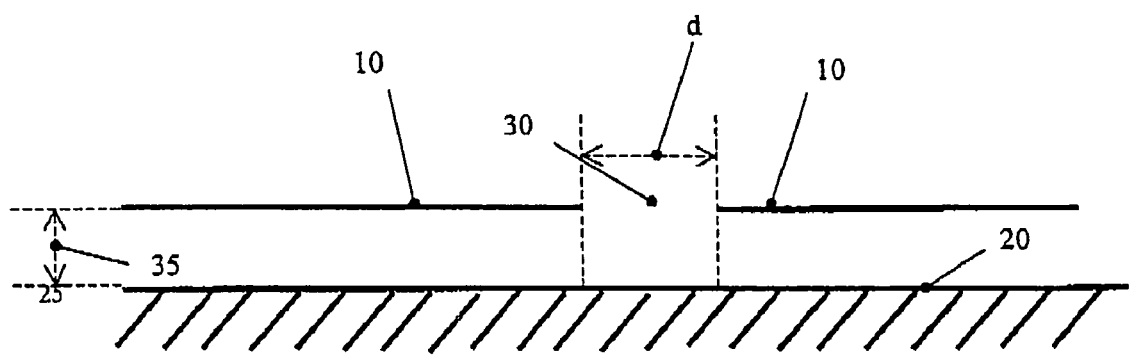
FIG. 4: a schematic representation of the relevant dimensions in an em-bodiment of the present invention.

FIGS. 2–4 illustrate schematically the principle of the present invention: The primary beam is passing through an aperture opening 30 of a shielding electrode 10. The dimensions of the aperture 30 are as small as possible without limiting the primary beam scan field. In addition, the shielding electrode 10 is positioned so close to the sample surface 20 that it effectively shields any electrical fields 3 which might exist or arise by sample surface charges 4 outside the aperture opening. This is shown in FIG. 3. For a better comparison with FIG. 1, surface charges 4 and the resulting lines 3 of the electric flux are for the sake of simplicity only shown for the region left of the impact point of the primary beam 1.

A part of the secondary particle beam 2 passes through the opening 30 of the shielding electrode 10 and reaches the detector 50. The detector signal in combination with the information of primary beam landing position is used to generate the image. Only surface charges 4 within a certain area around the center of the electrode opening 30 can contribute to primary beam shifting, leading to false information of the primary beam landing position, and therefore leading to a distortion of the generated image. The shielding electrode 10 is so closely arranged to the primary beam 1 landing position on the sample surface 20 that the secondary or higher order particles are prevented from reaching regions outside the aperture opening 30. However, to this end it is not necessary that the shielding electrode 10 is completely covering the region outside its opening 30. Preferably, the outer dimension d' of the shielding electrode (cf. FIG. 5a) is equal or greater than 0,2 mm, preferably more than 2 mm. Depending on the distance of the final optical element (e.g. the final lens) to the sample surface (e.g. working distance), the outer diameter d' can also have values of more than 5 mm or even 10 mm.

The remaining charges in a region inside the FOV, where the electrode 10 has no shielding effect can contribute to the charging effect. However, if this region is small enough, depending on uniformity and magnitude of remaining charge build up, the effect on the primary beam landing position or on the secondary beam properties such as energy or emission angle is small enough. As a result, there is only a negligible influence on the quality of the image recorded by the detector 50 of the scanning electron microscope.

The present invention discloses a solution, which is passive in its working principle, in contrast to many of the above discussed prior art approaches, such as disclosed in U.S. Pat. No. 6,586,736. In other words, it is preferably independent of the specific scanning procedures, electrical conductance of the sample surface 20, or additional compensating particle beams. It does neither need varying voltages applied to the shielding electrode 10, nor does it need an electrode voltage other than zero, nor does it need more than one electrode 10, although all of these configurations may be chosen differently for specific tasks. In the preferred embodiment, the shielding electrode 10 is kept at a fixed potential, which may simply be achieved by grounding the electrode.

The apparatus according to the present invention can be used for the investigation and/or modification of any material, either conductive or insulating, any feature size, and any field of view as long as it is smaller than the free opening d of the aperture 30 (cf. FIG. 4). The latter is determined by the maximum tolerable influence length of asymmetrically surface charges and is typically below 100 microns. Values of up to 150 microns are also acceptable in certain situations, although lower values are preferred. For applications with high accuracy, such as CD-SEM, smaller openings are preferred having a diameter d of less than 50 microns or even less than 10 microns.

The distance 35 of the aperture plane to the sample surface 20 is also typically below 100 microns. However, also distances 35 of up to 250 microns are possible. The other extreme is to contact the sample surface 20 with the shielding electrode 10, which is possible as well, although not desirable in most cases for sample integrity. Preferred values of the distance 35 are below 50 microns or even below 10 microns. Further, it has been found that the diameter d of the opening 30 is preferably greater or equal to the distance 35 between the shielding electrode 10 with the opening 30 and the surface 20 of the sample. The shielding element 10 has preferably a thickness of $\leq 100\,\mu m$, preferably 10–50 μm and more preferably $\leq 10\,\mu m$.

The physical principles of reducing charging effects employed by this invention are preferably: (a) the suppression of secondary particles (generated by the primary beam) landing on the sample in regions outside the interesting FOV, and (b) the shielding of electrical fields generated by accumulated charges in regions outside the interesting FOV. Due to the introduction of an aperture 30, electric fields generated by surface charges outside the FOV are essentially terminated at the aperture surface 10 and do not influence the trajectories of the primary or secondary beam above the aperture plane. The primary beam 1 and the secondary beam 2 might still be affected by (a) charges accumulated inside the aperture opening and (b) by electric fringe fields below the aperture plane. The first effect can be minimized by reducing the aperture opening 30, the latter by reducing the distance 35 between sample surface and aperture plane. Therefore, the present invention can suppress charge accumulation effects to any limit required by making the aperture opening 30 sufficiently small and positioning the shielding electrode 10 with its opening 30 sufficiently close to the sample surface 20. This allows for the first time to study or modify even thick insulators, where the penetration depth of the electron beam is shorter than the thickness of the insulator.

The shielding electrode 10 comprises an easy to generate aperture 30, which is in one embodiment a circular opening (cf. FIG. 5a), which is located at a distance 35 of about 100 microns or less above the sample surface (cf. FIG. 4). The diameter d of this opening is small enough so that the remaining charging effects are small enough for the desired image quality and accuracy (e.g. d is in the order of a few hundred microns or less). This embodiment is usually sufficient for an image quality to be expected from present art scanning electron microscopy.

In another embodiment, which is schematically illustrated in FIGS. 5b and 5c, the shielding electrode 10 comprises a fine meshed conductive grid 11. A preferred mesh is for example 700 pitch per inch with a total transmissivity T of around 50% and a thickness of 10 μm. Other values are also possible, for example a grid with only 200 pitch per inch and values for T ranging from 30% to 80%. Also the thickness of the grid may vary from 1–30 microns.

The grid 11 is positioned about 50 μm above the sample surface 20 and is held at a fixed potential, preferably ground potential. The primary electron beam 1, having an energy between a few hundred volts and a few kilovolts, is passing through one of the free squares 15 of the grid, releasing secondary electrons off the sample surface. The shielding effect of the grid 11 is comparable to the embodiment of FIG. 5a, however, the operator's navigation is facilitated by the grid structure, as it shows a larger amount of surface 20 and not only the section below the opening 30. Further, the grid 11 allows a better access of process gases (not shown) to the sample surface 20. The latter is particularly important for sample surface 20 modification by charged particle beam induced chemical reactions and can be influenced by the transmissivity T of the grid 11.

FIGS. 6a and 6b illustrate another important application of the present invention, wherein the electron beam is used to selectively deposit material on or remove material from the surface, for example for the repair of costly masks used in photolithography for the manufacture of semiconductor devices. The deposition is achieved by bringing precursor substances 91 into the vicinity of the surface, such as suitable organo-metallic compounds, which are selectively decomposed by the electron beam 1. It is apparent that the resolution of this technique will be affected, if the beam 1 is deviated or defocused due to charges accumulating on the surface of the sample.

In the embodiment of FIG. 6a, an additional gas supply 90 is provided above the aperture 30. The distance of the gas supply 90 from the aperture 30 and the size of the latter are preferably selected such that sufficient molecules or atoms 91 can reach the surface 20 through the aperture 30.

FIG. 6b discloses a further embodiment, wherein the shielding electrode 10 comprises a very small, preferably rectangular opening 30 in a thin membrane 12. The membrane surface is conductive and the membrane 12 is preferably fixed to a supporting structure 60 (e.g. a silicon wafer), as it is commonly used in transmission electron microscopy. The foil or membrane 12 is perforated (for example by electron beam lithography, focussed ion beam (FIB) or laser beam micromachining), thus representing an aperture 30 of preferably 10 microns or less in size. The aperture opening shape can be adjusted in such a way as to optimize the primary beam scan field with maximum shielding efficiency. Structures of the type shown in FIG. 6b are very flat and can be brought into the closest vicinity of the sample surface, with distances of for example less than 20 microns. This type of embodiment offers highest precision primary beam positioning accuracy without touching the sample surface.

The embodiment of FIG. 6b is particularly suitable for the surface modification by SEM electron beam induced chemical reactions as described above. Here the short distance between the shielding electrode 10 and the surface 20 in combination with a very small opening 30 allows aspect ratios (sample-electrode distance to opening size) of about unity. One or more process gas inlets 90 can be integrated into the supporting structure 60, for example by standard MEMS-technology. A gas inlet below the shielding electrode has the further advantage that the gas pressure at the sample surface 20 is higher without deteriorating the overall pressure of the vacuum in the measurement chamber above the shielding electrode 10. The embodiment of FIG. 6b allows an electron beam induced chemical surface modification with a precision in the range of a few nanometers.

In a further embodiment (not shown) the opening in the shielding electrode is a lengthy slit, wherein one dimension of the opening is much larger than the other dimension, the smaller dimension being sufficiently small (e. g. smaller than 100 microns) to ensure proper functionality, the larger dimension being large enough to allow the full scan length for the beam. The smaller dimension has values as indicated above for the dimension d of the other embodiments. This alternative is especially valuable in electron beam raster scan writing tools, which are employed in the semiconductor process industry.

In another embodiment the electrode comprises multiple openings of any of the types described above. This is especially valuable for multi-beam exposure systems, as they are increasingly under development for increasing working speed (e.g. wafer inspection time, or mask writing time) in parallel beam systems.

In the described SEM-application the electrons have preferably a sufficient energy for a secondary electron coefficient of >1. This leads to a positive charge on the sample surface, which can than be effectively shielded by the electrode 10. To this end the energy E of the electrons is preferably below 5 keV. However, if the primary beam is a beam of electrons of such an energy that the secondary electron emission coefficient is less than unity, leading to negative charge build-up on the sample surface, an additional beam of photons or low energy electrons (with an energy sufficient for a secondary electron coefficient of >1) can be focussed onto the same spot as the primary electron beam. This additional beam overcompensates the high negative charge caused by the primary beam, resulting in a low positive charge at the surface. Without limiting the scope of the present invention to low energy beams, this method may be applied in addition to the described invention to further minimize adverse effects of charge accumulation for higher energy electron beams.

The invention claimed is:

1. Apparatus for investigating and/or modifying a sample with charged particles, in particular a scanning electron microscope, said sample having a sample surface, comprising:
   a. a beam of charged particles;
   b. an electrically conductive shielding element having an opening for the beam of charged particles to pass through;
   c. wherein the shielding element is located a distance above the sample so that the shielding element does not contact the sample;
   d. wherein the distance between the shielding element and the sample surface is smaller than 50 microns; and
   e. wherein the opening in the shielding element has a dimension in at least one direction of less than 50 microns.

2. Apparatus of claim 1, wherein said shielding element has at least one further opening to which a gas supply is connected.

3. Apparatus according to claim 1, wherein the opening has a diameter d, wherein d $\leq$ 10 µm.

4. Apparatus according to claim 1, wherein the distance between the shielding element and the surface of the sample is $\leq$ 10 µm.

5. Apparatus according to claim 1, wherein the shielding element has an outer dimension d' of $\geq$ 0,2 mm, preferably $\geq$ 2 mm, more preferably $\geq$ 5 mm and most preferably $\geq$ 10 mm.

6. Apparatus according to claim 1, wherein the shielding element has a thickness of $\leq$ 100 µm, preferably 10–50 µm, more preferably $\leq$ 10 µm.

7. Apparatus according to claim 1, wherein the beam is scanned over the surface of the sample and wherein the opening has a shape corresponding to the part of the surface, which is scanned.

8. Apparatus according to claim 1, wherein the opening has a substantially rectangular or hexagonal or trigonal shape.

9. Apparatus according to claim 1, wherein the opening has a slit-like shape and wherein the slit has the width d.

10. Apparatus according to claim 1, wherein the electrons have an energy below 5 keV.

11. Apparatus according to claim 1, wherein the shielding element further comprises a distance sensor.

12. Apparatus for investigating and/or modifying a sample with charged particles, in particular a scanning electron microscope, said sample having a sample surface comprising:
   a. a beam of charged particles;
   b. an electrically conductive shielding element having an opening for the beam of charged particles to pass through;
   c. wherein the shielding element is located a distance above the sample so that the shielding element does not contact the sample;
   d. wherein the distance between the shielding element and the sample surface is smaller than 50 microns; and
   e. wherein the shielding element comprises a conductive grid, where the grid has a pitch of more than 200 per inch or a transmission in the range between 30% and 80% or has a thickness in the range between 1 micron and 30 microns.

13. Apparatus of claim 12, wherein said shielding element has at least one further opening to which a gas supply is connected.

14. Apparatus according to claim 12, wherein the shielding element has an outer dimension d' of $\geq$ 0,2 mm, preferably $\geq$ 2 mm, more preferably $\geq$ 5 mm and most preferably $\geq$ 10 mm.

15. Apparatus according to claim 12, wherein the shielding element has a thickness of $\leq$ 100 µm, preferably 10–50 µm, more preferably $\leq$ 10 µm.

16. Apparatus according to claims 12, wherein the beam is scanned over the surface of the sample and wherein the opening has a shape corresponding to the part of the surface, which is scanned.

17. Apparatus according to claim 12, wherein the opening has a substantially rectangular or hexagonal or trigonal shape.

18. Apparatus according to claim 12, wherein the electrons have an energy below 5 keV.

19. Apparatus according to claim 12, wherein the shielding element further comprises a distance sensor.

20. Apparatus for investigating and/or modifying a sample with charged particles, in particular a scanning electron microscope, said sample having a sample surface comprising:
   a. a beam of charged particles;
   b. an electrically conductive shielding element having an opening for the beam of charged particles to pass through;
   c. wherein the shielding element is located a distance above the sample so that the shielding element does not contact the sample;
   d. wherein the shielding element is a conductive membrane attached to a supporting structure, and
   e. wherein the distance between the shielding element and the sample surface is smaller than 50 microns.

21. Apparatus of claim 20, wherein said shielding element has at least one further opening to which a gas supply is connected.

22. Apparatus according to claim 20, wherein the shielding element has an outer dimension d' of $\geq$ 0,2 mm, preferably $\geq$ 2 mm, more preferably $\geq$ 5 mm and most preferably $\geq$ 10 mm.

23. Apparatus according to claim 20, wherein the electrons have an energy below 5 keV.

24. Apparatus according to claim 20, wherein the shielding element further comprises a distance sensor.

25. Method for investigating and/or modifying a sample, said sample having a sample surface, using an apparatus, in particular a scanning electron microscope, comprising:
   a. a beam of charged particles;
   b. an electrically conductive shielding element having an opening for the beam of charged particles to pass through;
   c. wherein the shielding element is located a distance above the sample so that the shielding element does not contact the sample;
   d. wherein the distance between the shielding element and the sample surface is smaller than 50 microns; and e. wherein the opening in the shielding element has a dimension in at least one direction of less than 50 microns.

26. Method according to claim 25, wherein the apparatus is used for the repair of a mask as used in the semiconductor industry, in particular for the selective removal and/or deposition of material from or on the mask, respectively.

27. Method according to claim 25, wherein the apparatus is used for CD-SEM measurements.

28. Method for investigating and/or modifying a sample, said sample having a sample surface, using an apparatus, in particular a scanning electron microscope, comprising:
   a. a beam of charged particles;
   b. an electrically conductive shielding element having an opening for the beam of charged particles to pass through;
   c. wherein the shielding element is located a distance above the sample so that the shielding element does not contact the sample;
   d. wherein the distance between the shielding element and the sample surface is smaller than 50 microns; and
   e. wherein the shielding element comprises a conductive grid, where the grid has a pitch of more than 200 per inch or a transmission in the range between 30% and 80% or has a thickness in the range between 1 micron and 30 microns.

29. Method according to claim 28, wherein the apparatus is used for the repair of a mask as used in the semiconductor industry, in particular for the selective removal and/or deposition of material from or on the mask, respectively.

30. Method according to claim 28, wherein the apparatus is used for CD-SEM measurements.

31. Method for investigating and/or modifying a sample, said sample having a sample surface, using an apparatus, in particular a scanning electron microscope, comprising:
   a. a beam of charged particles;
   b. an electrically conductive shielding element having an opening for the beam of charged particles to pass through;
   c. wherein the shielding element is located a distance above the sample so that the shielding element does not contact the sample;
   d. wherein the shielding element is a conductive membrane attached to a supporting structure, and
   e. wherein the distance between the shielding element and the sample surface is smaller than 50 microns.

32. Method according to claim 31, wherein the apparatus is used for the repair of a mask as used in the semiconductor industry, in particular for the selective removal and/or deposition of material from or on the mask, respectively.

33. Method according to claim 31, wherein the apparatus is used for CD-SEM measurements.

34. Mask, in particular for photolithography, processed by a method using an apparatus, in particular a scanning electron microscope, for investigating and/or modifying the mask with charged particles, said mask having a mask surface, the apparatus comprising:
   a. a beam of charged particles;
   b. an electrically conductive shielding element having an opening for the beam of charged particles to pass through;
   c. wherein the shielding element is located a distance above the mask so that the shielding element does not contact the mask;
   d. wherein the distance between the shielding element and the mask surface is smaller than 50 microns; and
   e. wherein the opening in the shielding element has a dimension in at least one direction of less than 50 microns.

35. Mask, in particular for photolithography, processed by a method using an apparatus, in particular a scanning electron microscope, for investigating and/or modifying the mask with charged particles, said mask having a mask surface, the apparatus comprising:
   a. a beam of charged particles;
   b. an electrically conductive shielding element having an opening for the beam of charged particles to pass through;
   c. wherein the shielding element is located a distance above the mask so that the shielding element does not contact the mask;
   d. wherein the distance between the shielding element and the mask surface is smaller than 50 microns; and
   e. wherein the shielding element comprises a conductive grid, where the grid has a pitch of more than 200 per inch or a transmission in the range between 30% and 80% or has a thickness in the range between 1 micron and 30 microns.

36. Mask, in particular for photolithography, processed by a method using an apparatus, in particular a scanning electron microscope, for investigating and/or modifying the mask with charged particles, said mask having a mask surface, the apparatus comprising:
   a. a beam of charged particles;
   b. an electrically conductive shielding element having an opening for the beam of charged particles to pass through;
   c. wherein the shielding element is located a distance above the mask so that the shielding element does not contact the mask;
   d. wherein the shielding element is a conductive membrane attached to a supporting structure, and
   e. wherein the distance between the shielding element and the sample surface is smaller than 50 microns.

* * * * *